United States Patent
Brandner et al.

(10) Patent No.: US 10,651,480 B2
(45) Date of Patent: May 12, 2020

(54) POWDER METALLURGICAL MOLDING AND METHOD OF PRODUCING SAME

(71) Applicant: PLANSEE SE, Reutte (AT)

(72) Inventors: Marco Brandner, Waltenhofen (DE); Michael O'Sullivan, Ehenbichl (AT); Thomas Leiter, Reutte (AT); Oliver Hirsch, Berwang (AT); Wolfgang Kraussler, Weissenbach (AT)

(73) Assignee: Plansee SE, Reutte (AT)

(*) Notice: Subject to any disclaimer, the term of this patent is extended or adjusted under 35 U.S.C. 154(b) by 161 days.

(21) Appl. No.: 15/057,546

(22) Filed: Mar. 1, 2016

(65) Prior Publication Data

US 2016/0181624 A1 Jun. 23, 2016

Related U.S. Application Data

(63) Continuation of application No. PCT/AT2014/000158, filed on Aug. 19, 2014.

(30) Foreign Application Priority Data

Sep. 2, 2013 (AT) .............................. GM282/2013

(51) Int. Cl.
*H01M 8/0202* (2016.01)
*H01M 8/026* (2016.01)
(Continued)

(52) U.S. Cl.
CPC ......... *H01M 8/0202* (2013.01); *B22F 1/0003* (2013.01); *B22F 3/16* (2013.01);
(Continued)

(58) Field of Classification Search
CPC ............ H01M 8/0206; H01M 8/0247; H01M 8/0258; H01M 8/1246; H01M 8/0202;
(Continued)

(56) References Cited

U.S. PATENT DOCUMENTS 5,034,288 A 7/1991 Bossel
5,407,758 A 4/1995 Greiner et al.
(Continued)

FOREIGN PATENT DOCUMENTS

EP 0378812 A1 7/1990
EP 0629015 A1 12/1994
(Continued)

OTHER PUBLICATIONS

Wikipedia contributors, "Significant figures," Wikipedia, The Free Encyclopedia, https://en.wikipedia.org/w/index.php?title=Significant_figures&oldid=898603536 (accessed Jun. 11, 2019). (Year: 2019).*

*Primary Examiner* — Sean P Cullen
(74) *Attorney, Agent, or Firm* — Laurence A. Greenberg; Werner H. Stemer; Ralph E. Locher

(57) ABSTRACT

A powder metallurgical molding forms an interconnector or an end plate for an electrochemical cell. The molding has a chromium content of at least 80% by weight, a basic shape of a plate and one or more flow fields with structuring formed on one or both of the main faces of the molding. A ratio of a maximum diameter $D_{max}$ of the molding, measured along the main face, to a minimum thickness $d_{min}$ of a core region of the molding which extends along the flow field or fields and is not affected by the structuring lies in a range of $140 \leq D_{max}/d_{min} \leq 350$.

18 Claims, 2 Drawing Sheets

(51) Int. Cl.

| | | |
|---|---|---|
| B22F 5/00 | (2006.01) | |
| C22C 32/00 | (2006.01) | |
| H01M 8/0206 | (2016.01) | |
| H01M 8/0247 | (2016.01) | |
| C22C 1/10 | (2006.01) | |
| C22C 1/04 | (2006.01) | |
| C22C 1/08 | (2006.01) | |
| B22F 9/20 | (2006.01) | |
| B22F 1/00 | (2006.01) | |
| B22F 3/16 | (2006.01) | |
| B22F 3/24 | (2006.01) | |
| C22C 27/06 | (2006.01) | |
| C23C 8/02 | (2006.01) | |
| C23C 8/10 | (2006.01) | |
| C23C 8/80 | (2006.01) | |
| H01M 8/1246 | (2016.01) | |
| H01M 8/124 | (2016.01) | |

(52) U.S. Cl.
CPC ............... *B22F 3/24* (2013.01); *B22F 5/006* (2013.01); *B22F 9/20* (2013.01); *C22C 1/045* (2013.01); *C22C 1/08* (2013.01); *C22C 1/1078* (2013.01); *C22C 27/06* (2013.01); *C22C 32/0026* (2013.01); *C23C 8/02* (2013.01); *C23C 8/10* (2013.01); *C23C 8/80* (2013.01); *H01M 8/0206* (2013.01); *H01M 8/026* (2013.01); *H01M 8/0247* (2013.01); *H01M 8/1246* (2013.01); *B22F 2003/242* (2013.01); *B22F 2005/005* (2013.01); *B22F 2201/03* (2013.01); *B22F 2301/20* (2013.01); *B22F 2998/10* (2013.01); *B22F 2999/00* (2013.01); *H01M 2008/1293* (2013.01)

(58) Field of Classification Search
CPC ........... H01M 8/026; B22F 5/006; B22F 9/20; B22F 3/24; B22F 3/16; B22F 1/0003; C22C 1/045; C22C 1/08; C22C 1/1078; C22C 32/0026; C22C 27/06; C23C 8/80; C23C 8/10; C23C 8/02
USPC .............................. 429/508; 204/279; 419/26
See application file for complete search history.

(56) References Cited

U.S. PATENT DOCUMENTS

| | | | |
|---|---|---|---|
| 5,578,388 A | 11/1996 | Faita et al. | |
| 5,942,347 A * | 8/1999 | Koncar | H01M 8/023 |
| | | | 264/105 |
| 6,280,868 B1 | 8/2001 | Badwal et al. | |
| 6,322,919 B1 * | 11/2001 | Yang | H01M 8/0228 |
| | | | 429/457 |
| 6,794,078 B1 * | 9/2004 | Tashiro | H01M 8/0226 |
| | | | 29/623.1 |
| 7,390,456 B2 | 6/2008 | Glatz et al. | |
| 9,029,044 B2 | 5/2015 | Brandner et al. | |
| 9,472,816 B2 | 10/2016 | Brandner et al. | |
| 2003/0180597 A1 * | 9/2003 | Sakamoto | H01M 8/0213 |
| | | | 429/465 |
| 2004/0214066 A1 * | 10/2004 | Hatoh | H01M 8/0206 |
| | | | 429/492 |
| 2005/0053819 A1 * | 3/2005 | Paz | H01M 4/90 |
| | | | 429/425 |
| 2006/0192323 A1 | 8/2006 | Zobl et al. | |
| 2008/0044711 A1 * | 2/2008 | Grafl | C09D 5/24 |
| | | | 429/482 |
| 2008/0199738 A1 | 8/2008 | Perry et al. | |
| 2009/0117441 A1 * | 5/2009 | Suzuki | B30B 11/02 |
| | | | 429/535 |
| 2010/0233576 A1 | 9/2010 | Brandner et al. | |
| 2011/0135531 A1 | 6/2011 | Hsu et al. | |
| 2011/0143261 A1 | 6/2011 | Brandner et al. | |
| 2013/0129557 A1 * | 5/2013 | Herchen | H01M 8/0202 |
| | | | 419/62 |
| 2013/0130152 A1 * | 5/2013 | Couse | H01M 8/0258 |
| | | | 429/508 |
| 2014/0147692 A1 | 5/2014 | Brandner et al. | |

FOREIGN PATENT DOCUMENTS

| | | |
|---|---|---|
| EP | 2230707 A1 | 9/2010 |
| JP | 2004517215 A | 6/2004 |
| JP | 2010219045 A | 9/2010 |
| JP | 2011249146 A | 12/2011 |
| JP | 2014525988 A | 10/2014 |
| WO | 9735349 A1 | 9/1997 |
| WO | 2008103253 A1 | 8/2008 |
| WO | 2013010198 A1 | 1/2013 |

\* cited by examiner

POWDER METALLURGICAL MOLDING AND METHOD OF PRODUCING SAME

CROSS-REFERENCE TO RELATED APPLICATION

This application is a continuation, under 35 U.S.C. § 120, of copending international application PCT/AT2014/000158, filed Aug. 19, 2014, which designated the United States; this application also claims the priority, under 35 U.S.C. § 119, of Austrian application No. GM 282/2013, filed Sep. 2, 2013; the prior applications are herewith incorporated by reference in their entirety.

BACKGROUND OF THE INVENTION

Field of the Invention

The present invention relates to a powder metallurgical molding forming an interconnector or an end plate for an electrochemical cell. The molding has a chromium content of at least 80% by weight, a plate-like basic shape and (a) flow field(s) formed on one or both of the main faces of the molding. A main face has in the region of the flow field/fields a structuring formed in the molding with a plurality of knob-shaped or ridge-shaped elevations and intermediate depressions. The present invention relates further to a process for the production of such a powder metallurgical molding.

Solid oxide fuel cells (SOFCs) and other electrochemical cells of similar construction, such as, for example, solid oxide electrolyzer cells (SOECs), are designed for relatively high operating temperatures (e.g. in the case of electrolyte-supported electrochemical cells typically in the range of from 700° C. to 950° C.). There are known inter alia electrochemical cells (SOFCs, SOECs) which have a ceramic solid electrolyte plate (e.g. based on zirconium oxide with small added amounts of yttrium oxide or scandium oxide) with electrodes (anode, cathode) formed on both sides. The electrochemical cells are frequently in the form of planar individual elements and are stacked one above the other to form a stack. Within the stack, the process gases are to be conducted to the individual electrochemical cells, the process gases of adjacent electrochemical cells are to be separated, and electrical contacting between adjacent electrochemical cells is to be achieved. In order to provide those functions, interconnectors are used between the individual electrochemical cells of a stack, and the stack itself is generally terminated by end plates, which provide the mentioned functions on only one side and may have corresponding connection options on the other side. In fuel cell applications, conduction of the process gases includes, for example, the supply of combustion gas on the anode side, the supply of oxygen (e.g. air) on the cathode side, and the discharge on the anode side and on the cathode side of the gases that are formed.

Interconnectors and end plates must further have a thermal expansion coefficient which is adapted to the electrochemical cell (in particular to the solid electrolyte) and also high corrosion resistance. Starting from those requirements, Cr-based alloys (i.e. Cr content ≥50% by weight, in particular Cr content ≥80% by weight, see e.g. U.S. Pat. No. 5,407,758 A) have been found to be suitable. In the production of interconnectors and end plates, the manufacturing route by powder metallurgy, which comprises at least the steps of pressing a corresponding powder batch and sintering, has become established. It is distinguished inter alia by comparatively low production costs.

Depending on the field of application, the volumetric and optionally also the gravimetric power density (i.e. the power per unit volume or the power per unit weight) of the electrochemical system, which comprises a plurality of electrochemical cells and interconnectors arranged there between (and optionally also end plates provided at the ends), constitutes an important criterion. Interconnectors produced by powder metallurgy in their structural forms known hitherto are relatively thick and occupy, for example in the case of electrolyte-supported electrochemical cells, approximately 15 times as much space as the individual electrochemical cells. The relatively thick form of conventional powder metallurgical interconnectors and end plates is determined inter alia by the following factors:

a) provision of flow field(s) with structuring(s) on one or both main face(s);
b) provision of sufficient stability of the molding;
c) achievement of a uniform temperature distribution over the molding; and
d) provision of a reliable manufacturing route.

SUMMARY OF THE INVENTION

It is accordingly an object of the invention to provide a powder-metallurgical molding and a production method which overcome a variety of the above and other disadvantages of the heretofore-known devices and methods of this general type and which optimize interconnectors and end plates further in view of the achievement of a maximum volumetric and gravimetric power density of the associated electrochemical system, whereby low component costs for the interconnectors and end plates are desired at the same time.

With the foregoing and other objects in view there is provided, in accordance with the invention, a powder metallurgical molding for an electrochemical cell, the molding comprising:

a plate having a basic plate shape with two main faces;
the plate being formed with a chromium content of at least 80% by weight;
one or both of said main faces having:
a flow field formed on one or both of said main faces, said main face having, in the region of said flow field, a structuring with a plurality of knob-shaped or ridge-like elevations and intermediate depressions;
wherein a ratio of a maximum diameter $D_{max}$ of the molding, measured along the main face, to a minimum thickness $d_{min}$ of a core region of the molding that extends along the flow field(s) and is not affected by the structuring lies in a range of $140 \leq D_{max}/d_{min} \leq 350$.

In other words, according to the present invention there is provided a powder metallurgical molding which forms an interconnector or an end plate for an electrochemical cell. The molding has a chromium content of at least 80% by weight, a plate-like basic shape and (a) flow field(s) formed on one or both of the main faces of the molding. The main face has in the region of the flow field(s) a structuring formed in the molding with a plurality of knob- or ridge-like elevations and intermediate depressions. A ratio of the maximum diameter $D_{max}$ (in mm) of the molding, measured along the main face, to a minimum thickness $d_{min}$ (in mm) of a core region of the molding which extends along the flow field(s) and is not affected by the structuring(s) is in the range $140 \leq D_{max}/d_{min} \leq 350$.

Within that range, the moldings are thinner compared with powder metallurgical interconnectors and end plates known hitherto relative to their maximum diameter.

As a result, a higher volumetric and gravimetric power density can be achieved for the associated electrochemical system (consisting of a plurality of electrochemical cells and interconnectors and also optionally of end plates provided at the ends). A further advantage is that the material costs incurred for the individual molding are reduced.

By means of such a relative (i.e. in relation to the maximum diameter $D_{max}$) reduction of the thickness of the core region, a relatively high structural depth of the structuring(s) of the flow field/fields can be retained. As a result, a comparatively large flow cross-section for the process gases is provided, which in turn is advantageous for the conduction of the process gases (because a smaller pressure loss occurs over the length of the channel). Preferably, the structural depth is ≥0.5 mm, the structural depth on the main face facing the cathode preferably being deeper (e.g. ≥0.8 mm) than the structural depth on the main face facing the anode (e.g. ≥0.5 mm). The claimed range for the ratio $D_{max}/d_{min}$ is therefore a highly suitable value for defining the proportions of the molding, because it is a parameter that is independent of the external shape and the absolute overall size of the molding and because it has been shown that, for reasons of stability of the molding (see criterion b) above) and on account of the production-related framework conditions (see criterion d) above) during production by powder metallurgy, the thickness of the core region should increase as the size of the molding increases. The maximum value of the claimed range for the ratio $D_{max}/d_{min}$ is so chosen that there is still sufficient stability and a largely uniform temperature distribution is ensured over the molding (see criteria b) and c) above).

In relation to maximum possible stability of the moldings it is to be noted that there were used hitherto for the manufacture of interconnectors and endplates by powder metallurgy generally chromium powders or chromium-containing powders produced by a comparatively inexpensive, aluminothermic process. Aluminothermic processes start from finely divided aluminum powder, which is mixed carefully with chromium oxide. The reaction mixture is then ignited, as a result of which the chromium oxide is reduced to metallic chromium while the metallic aluminum is oxidized to $Al_2O_3$. The resulting reaction product is melted, liquid chromium settling and slag with $Al_2O_3$ as the main constituent floating on the liquid chromium. After cooling and solidification, the slag is separated mechanically from the pure chromium metal, and the metal is broken into lumps and ground to the desired particle size or particle size distribution in order to obtain the chromium metal powder, it also being possible for this operation to be followed by sieving operations. The powder so obtained, which is conventionally used to manufacture the moldings, is coarse and angular—if no additional processing steps for increasing the surface area have been carried out—and has almost no inner porosity. Although the use of such a powder (optionally in combination with further powders, pressing aids, etc.) permits comparatively high compressed densities, it has been shown that the stability of the pressed green compact and also of the sintered molding is comparatively low when such powders are used. This is attributed to only moderate bonding between the individual particles and also to a relatively uneven distribution of the residual porosity. The sintered moldings produced from such powders contain individual, comparatively large pores. Accordingly, the moldings defined according to the invention can generally not be produced with sufficient stability using the powders described above.

It has been shown that if, in the operation of producing the molding by powder metallurgy, at least a portion of the chromium-containing powder has a BET surface area of ≥0.05 m$^2$/g, significantly higher stability of the pressed green compact and also of the sintered molding can be achieved. The data relating to the BET surface area within the context of this application relate to a BET measurement according to standard (ISO 9277:1995, measurement range: 0.01-300 m$^2$/g; instrument:

Gemini II 2370, heating temperature: 130° C., heating time: 2 hours; adsorptive: nitrogen, volumetric evaluation by five-point determination). The use of such a powder allows the moldings defined according to the invention to be produced with particularly high stability. Accordingly, the present invention relates also to a powder metallurgical molding as claimed which can be produced by the process defined herein, in particular which has been produced by the process described and claimed herein. As is described in relation to further developments and variants of the present invention, such a chromium-containing powder can be produced from conventional powders (e.g. produced by aluminothermic means) by processing steps for increasing the surface area or also by a production method in which at least one compound from the group consisting of chromium oxide and chromium hydroxide, optionally with an added solid carbon source, is reduced under the at least temporary exposure of hydrogen and hydrocarbon. The powder so produced has a sponge-like structure and can be compressed particularly well and densely (even at relatively low pressing pressures), good interlocking between the particles being achieved. As a result, the molding can be relieved of pressure again once the maximum pressure has been reached without the occurrence of pitting. Furthermore, a high green strength of the green compacts and high stability of the sintered moldings are achieved.

The expression powder metallurgical molding denotes a component produced in the described shape (i.e. including the structuring(s)) by pressing powder(s) and by subsequent sintering, it also being possible to provide further treatment steps, such as, for example, presintering after the pressing step and optionally also calibration pressing after the presintering step (and before the sintering step). The molding in its described shape (i.e. including the structuring(s)) is in a single piece and has the microstructure obtained within the context of production by powder metallurgy throughout. In particular, the described shape is achieved solely by correspondingly formed pressing tools, and no subsequent shaping processing step is carried out. The microstructure obtained within the context of production by powder metallurgy is formed as a result of the fact that, as the sintering process progresses by solid diffusion, the particles densified by pressing are bonded together by sinter necks, which become increasingly thicker, while the voids between the particles become increasingly smaller. There is a random distribution of the size and position of the pores. A "powder metallurgical molding" can be recognized by a person skilled in the art by metallurgical examination methods (e.g. formation of a ground section on a cross-sectional surface and examination by a scanning electron microscope). The powder metallurgical molding can be provided with further add-on parts, sealing portions and/or coatings, etc.

The composition of the molding is in particular within the following range:

a) Cr content (Cr: chromium) of ≥88% by weight and ≤98% by weight,
b) Fe content (Fe: iron) of ≥2% by weight and ≤12% by weight,
c) optional additions, e.g. Y addition (Y: yttrium) (e.g. 0.07% by weight Y).

In this manner it is possible to achieve high corrosion resistance and good adaptation of the thermal expansion coefficient to the material of the electrolyte, which is preferably formed of fully stabilized (e.g. with $Y_2O_3$ or $Sc_2O_3$) zirconium oxide (in particular in the case of electrolyte-supported electrochemical cells). According to a further development, the proportion of chromium (based on the total metal content) is ≥90% by weight. As the chromium content increases, the thermal conductivity is increased (homogeneous temperature distribution can be achieved) and the thermal expansion coefficient is lowered (better adaptation thereof to available electrolyte materials, such as, for example, fully stabilized zirconium oxide).

The molding is preferably formed by an interconnector which has at least one flow field on both of the main faces. The structuring(s) can be formed, for example, by a groove array with elongate elevations (in the form of, for example, ridges, ribs, etc.) arranged between the individual grooves, which elevations may also be broken one or more times along their main extension direction. Other types of structuring can also be suitable for conducting the process gases—as is known to the person skilled in the art.

The molding according to the invention (interconnector or end plate) is suitable for different types of solid-oxide-based electrochemical cells. It is preferably designed for electrolyte-supported electrochemical cells, in particular fuel cells. In the electrolyte-supported cell, the electrolyte forms the carrying component for the adjacent electrodes (and optionally further layers). According to a further development, the molding is designed for an electrolyte-supported electrochemical cell (in particular fuel cell) having fully stabilized (e.g. with $Y_2O_3$ or $Sc_2O_3$) zirconium oxide as the electrolyte. Such an electrolyte is distinguished by high ion conductivity and accordingly a high efficiency, but it is also very breakable, so that particularly good adaptation to the thermal expansion coefficient thereof is required. The claimed molding having the comparatively high chromium content (and also having the preferred composition range) is particularly suitable for that purpose. Different geometries are in principle possible for the shape of the main face, such as, for example, rectangular, square, diamond-shaped, parallelogram, circular, oval, etc., optionally also with one or more opening(s) within the main face. The main face is planar or substantially planar (i.e. it has only inclinations or waviness caused by pressing). The diameter is measured based on the bordering edges of the molding, regardless of whether one or more opening(s) are formed within the main face. It is also possible for there to be provided on a main face not only exactly one flow field but also a plurality of flow fields divided from one another. The thickness is measured perpendicular to the extension plane of the main face(s). According to the present invention, a core region that is not affected by the structuring(s) remains in the direction of the thickness in the region of the flow field/fields, that is to say a region which is not reached by the depressions protruding into the molding from one or both of the main faces. The thickness of this core region in the region of the flow field/fields can vary along the plane of the main face, and reference is accordingly made to the minimum thickness.

A minimum thickness of the molding at portions outside the flow field/fields may also be thinner or thicker.

In view of a further reduction of the material costs and optimization of the volumetric and gravimetric power density of the associated electrochemical system, it is preferred if the ratio $D_{max}/d_{min}$ is ≥150, in particular ≥180. In view of uniform temperature distribution and sufficient stability, on the other hand, it is advantageous if the ratio $D_{max}/d_{min}$ is ≤300, in particular ≤250.

According to a further development of the present invention, precisely one flow field is formed on both of the main faces of the molding. In particular, the core region is formed between the two mutually opposite structuring of the flow fields. According to a further development, an edge region which surrounds the flow field completely or partially (and is free of structuring(s) of the adjacent flow field) is provided on the respective main face. One or more (e.g. slot-like) through-opening(s) which serve to supply or convey away the process gases can additionally be provided in the edge region. Conduction of the process gases can also take place at least partially outside the extension surface of the interconnectors (along, for example, corresponding channels running on the outside) and the structuring in that case extend to the respective outside edge of the interconnector. It is also possible for both variants to be provided on one interconnector, for example on different side edges.

According to a further development, one or more flow fields are formed on both of the main faces of the molding and the structuring of mutually opposite flow fields have main extension directions (e.g. of the ridges, ribs, elongate knobs, channels, grooves, etc. of the structuring in question) which run substantially parallel to one another along the main faces (co-flow design). "Substantially parallel" refers to an exactly parallel course and alternatively also to an almost parallel course with deviations of up to ±10°. The co-flow design has the advantage, inter alia, that a preferred material flow and uniform material distribution can be achieved during the operation of pressing the molding. It is particularly preferred in this respect for the depressions of one main face to be arranged exactly or substantially opposite the elevations of the other main face and vice versa. The molding according to the invention can further be configured as an interconnector of cross-flow design, in which the main extension direction of the structuring of one flow field is oriented perpendicular or substantially perpendicular (i.e. deviations of up to ±10°) relative to the main extension direction of the structuring of a flow field arranged opposite. In addition, alternative orientations of mutually opposite flow fields are also possible, for example orientations which run obliquely relative to one another or also orientations which alternate over the main surface. It is further advantageous, in view of the operation of pressing the molding, if the flanks of the structuring(s) are each inclined in such a manner that the depressions taper towards their base on both sides (and the elevations correspondingly taper to their highest point on both sides).

According to a further embodiment, the molding has four circumferential side edges ("circumferential" about the respective main face), of which in each case two mutually opposite side edges run parallel to one another, the ratio of the side length $L_{max}$ of the longest side edge to the minimum thickness $d_{min}$ of the core region of the molding being ≥110. The described geometry of the molding is advantageous in particular for the structure of a stack and for process gas conduction (on the four circumferential sides). In particular, the molding has a rectangular, optionally also square, basic shape, and the ratio according to this further development is present. In view of a further reduction of the material costs and optimization of the power density, it is preferred if the ratio is ≥115, in particular ≥150. In view of uniform temperature distribution and sufficient stability, on the other hand, it is advantageous if the ratio is ≤220. Furthermore, in view of the total power of a stack, it is preferred if all the side lengths are ≥155 mm, in particular ≥170 mm.

According to a further development, the ratio of the size of the main face in mm$^2$ (square millimeters) to the minimum thickness d$_{min}$ of the core region of the molding in mm (millimeters) is ≥1.3×10$^4$. This ratio, irrespective of the geometry of the main face, is a suitable parameter for describing preferred geometric proportions of the molding, any openings provided in the main face (e.g. for process gas conduction) being included in the size of the main face. In view of the material costs and the total power of the stack, it is preferred if the ratio is ≥1.5×10$^4$, in particular ≥2.0×10$^4$. In view of uniform temperature distribution and sufficient stability, on the other hand, it is advantageous if the ratio is ≤3.5×10$^4$. According to a further development, the size of the main face is ≥240 cm$^2$ (square centimeters), preferably ≥280 cm$^2$, the size of the main face preferably being ≤500 cm$^2$ (square centimeters).

According to a further development, the ratio of the total weight of the molding in g (grams) to the size of the main face in cm$^2$ (square centimeters) is ≤1.1. Accordingly, a high gravimetric power density and a low material usage can be achieved. From this point of view it is particularly advantageous if the ratio is ≤1.0, in particular ≤0.9, it being preferred for stability reasons if the ratio is ≥0.7.

According to a further development, the maximum thickness (measured perpendicular to the extension plane of the main face(s)) of the molding in the region of the flow field/fields is ≤2.3 mm (millimeters), in particular ≤2.1 mm. In order to provide a sufficient flow cross-section for the process gases, the maximum thickness is preferably ≥1.6 mm. These limit values preferably also apply to the maximum thickness of the molding as a whole.

According to a further development, the minimum thickness d$_{min}$ of the core region of the molding is ≤1.1 mm (millimeters), in particular ≤1.0 mm, optionally even ≤0.9 mm. In view of sufficient stability, it is preferred if the minimum thickness is ≥0.7 mm. According to a further development, the maximum diameter of the molding, measured along the main face, is ≥200 mm. In view of a maximum total power of the stack, the maximum diameter of the molding, measured along the main face, is ≥220 mm, in particular ≥250 mm, a value ≤320 mm preferably being chosen for stability reasons.

According to a further development, in the core region, the proportion by surface area P of pores that are empty or partly filled with metal oxide(s) and of oxide inclusions, provided they lie wholly within the measurement area under consideration, relative to the total area of the measurement area, is in a range of 80%≤(1−P)≤95% (for the measuring method, see above). In the case of a material in which no metal oxides of Cr or further metals are formed, P would correspond to the porosity (evaluated by means of quantitative image analysis), it being possible according to the present invention for the (original) pores to be filled partly or completely with metal oxide(s). The pores filled with metal oxide(s) and also the oxide inclusions can purposively be introduced at least in part by subjecting the molding, after it has passed through the production route by powder metallurgy, to a subsequent oxidation process in order to minimize the open residual porosity. Because the Cr$_2$O$_3$ that forms or mixed oxides of Cr and Al (see US 2010/233576 A1) have a larger volume than the metallic matrix, so that the porosity can be closed up in the course of the oxidation process. It is not necessary for all the pores to the core of the molding to be filled with oxides, but at least an edge layer approximately 0.2 mm thick is closed. The resulting oxide layer on the surface of the molding is removed again in particular in a subsequent process at least in the region of the electrical contact faces, for example by a sand-blasting process, in order to ensure optimum metallic contact between the electrochemical cell and the interconnector or end plate at the start of operation. Accordingly, in the description of the microstructure of the molding, pores, pores partly filled with metal oxide(s), and oxide inclusions are in most cases combined. In the case of pores partly filled with metal oxide(s), the cross-sectional area thereof (within the context of quantitative image analysis) is calculated by adding together the partly filled portion and the empty portion. The main constituents of the "oxide inclusions" and also of the "metal oxide(s)" within the context of the invention are chromium oxides, the chromium oxide content preferably being at least 90% by weight. The "oxide inclusions" and "metal oxide(s)" can, however, also comprise metal oxides of further metals that are present and also metal nitrides of chromium and/or further metals that are present.

If, in the operation of producing the molding by powder metallurgy, at least a portion of the chromium-containing powder has a BET surface area of ≥0.05 m$^2$/g (square meters/gram), it is possible—as explained above—to achieve significantly higher stability and the powder can be pressed very well. In particular, the portion of the chromium-containing powder having a BET surface area of ≥0.05 m$^2$/g is ≥5% by weight, preferably ≥10% by weight, in each case based on the total amount of powder in the metal-containing powders (optionally elementary and/or present in the form of oxide, nitride, carbide, etc.) of the powder batch for the molding (wax as pressing aid is not included in the calculation in this respect, for example). Preferably, the entire chromium portion of the powder batch for the molding is provided by such a chromium-containing powder having a BET surface area of ≥0.05 m$^2$/g. In particular, the process steps as described are to be applied for the production of the molding. The use of such a powder is also recognizable from the advantageous microstructure of the molding, the preferred features of which will be explained herein below with reference to further developments. The microstructure is distinguished by very finely divided, very small pores. In comparison with moldings produced by conventional means, this allows the component thickness (in particular in the core region) to be reduced and/or the moldings to be made significantly larger (based on the main face thereof). The possibility is thereby also provided of manufacturing the molding to be gas-tight with a significantly reduced proportion of pore fillers (e.g. metal oxides, in particular chromium oxide, introduced by purposive oxidation) or optionally also by omitting the oxidation process, which on the one hand leads to physical properties which can better be controlled and on the other hand reduces the manufacturing costs. A powder having a BET surface area of ≥0.05 m$^2$/g can on the one hand be provided by carrying out processing steps for increasing the surface area on chromium powders or chromium-based powders produced by conventional means (e.g. by an aluminothermic process). For example, an increase in the surface area can be achieved by grinding such a conventional powder very finely, then agglomerating it (e.g. in a mixer or by spray agglomeration), and subsequently subjecting it to an annealing process (e.g. in a temperature range of from 800 to 1200° C. and for a period of approximately 1 h (hour)) and then sieving it. Particularly good properties of the molding, which are recognizable from its microstructure, are achieved if the powder having a BET surface area of ≥0.05 m²/g is produced according to the process steps as described. By means of such a process it is possible (without carrying out processing operations for increasing the surface area) in particular to produce a powder which has a BET value of ≥0.25 m²/g, in particular of up to 0.5 m²/g. The powder so produced has a sponge-like structure (of the individual particles) and can thus be pressed particularly well. In particular, lower pressing pressures are possible in comparison with conventional powder.

According to a further development, in the core region, the proportion by surface area of pores that are empty or partly filled with metal oxide(s) and of oxide inclusions which have a surface area of ≥100 µm² (square micrometers), relative to the total surface area of pores that are empty or partly filled with metal oxide(s) and of oxide inclusions, is ≤60%. These areas are evaluated by means of quantitative image analysis on a scanning electron microscope image of a measurement area located in a cut surface, running along the thickness direction, through the molding into the core region, the measuring method being explained in detail below (see "Description of the quantitative image analysis for determining the microstructure"). In particular, the proportion by surface area is ≤40%, preferably ≤10% and more preferably ≤7%, the lower values being preferred in relation to the stability and being achieved in particular (e.g. a proportion by surface area of 5% was achieved) when a powder produced according to the invention is used at least proportionately, in particular when the Cr portion is provided wholly by such a powder.

According to a further development, in the core region, the proportion by surface area of pores that are empty or partly filled with metal oxide(s) and of oxide inclusions which have a surface area of ≥70 µm² (square micrometers), relative to the total surface area of pores that are empty or partly filled with metal oxide(s) and of oxide inclusions, is ≤70% (for the measuring method see above). In particular, the proportion by surface area is ≤50%, preferably ≤20% and more preferably ≤17%, the lower values being preferred in relation to the stability and being achieved in particular (e.g. a proportion by surface area of 14% was achieved) when a powder produced as claimed is used at least proportionately, in particular when the Cr portion is provided wholly by such a powder produced according to the invention.

According to a further development, in the core region, the proportion by surface area of pores that are empty or partly filled with metal oxide(s) and of oxide inclusions which have a surface area of ≥50 µm² (square micrometers), relative to the total surface area of pores that are empty or partly filled with metal oxide(s) and of oxide inclusions, is ≤80% (for the measuring method see above). In particular, the proportion by surface area is ≤60%, preferably ≤30% and more preferably ≤27%, the lower values being preferred in relation to the stability and being achieved in particular (e.g. a proportion by surface area of 24% was achieved) when a powder produced as claimed is used at least proportionately, in particular when the Cr portion is provided wholly by such a powder produced according to the invention.

According to a further development, in the core region there is a uniform distribution of the pores that are empty or partly filled with metal oxide(s) and of the oxide inclusions (it being possible for the ratio between empty pores, partly filled pores and oxide inclusions to vary locally; for example—as is explained above—the proportion of metal oxide filling and of oxide inclusions relative to the empty pore volume can increase towards the surface of the molding) and the mean spacing λ of the pores that are empty or partly filled with metal oxide(s) and of the oxide inclusions is ≤9 µm, the mean spacing λ being calculated according to the formula $$\lambda = \left(\frac{\frac{4}{3}\pi a^3}{P}\right)^{\frac{1}{3}},$$

wherein 2a corresponds to the mean equivalent pore or oxide inclusion diameter (determined according to the formula wherein $$2a = \frac{\sum_{i=1}^{n}(2a_i)}{n},$$

"$2a_i$" is in each case the equivalent pore or oxide inclusion diameter of the pores that are empty or partly filled with metal oxide(s) and of oxide inclusions that lie wholly within the measurement area under consideration). Furthermore, P is the proportion by surface area of pores that are empty or partly filled with metal oxide(s) and of oxide inclusions, provided they lie wholly within the measurement area under consideration (for the measuring method for determining 2a and P by means of quantitative image analysis, see above). The equivalent pore or oxide inclusion diameter $2a_i$ is determined in the case of pores and oxide inclusions independently of the concrete cross-sectional shape, which is not necessarily circular, from the cross-sectional area A thereof according to the formula $2a_i=(4 A/\pi)^{0.5}$. In particular, the mean spacing λ is ≤7 µm, preferably ≤5 µm, the lower values being preferred in relation to the stability and being achieved in particular (e.g. λ=4 µm was achieved, λ typically being ≥2 µm) when a powder produced as claimed is used at least proportionately, in particular when the Cr portion is provided wholly by such a powder produced according to the invention.

In conventional aluminothermic powders, the mean spacing λ is typically 12.7 µm.

The features explained above which relate to the microstructure of the core region are preferably present throughout the entire core region of the molding in question. They are preferably present throughout the entire molding.

The present invention relates further to a process for the production of a powder metallurgical molding according to the invention which can optionally be configured according to one or more of the further developments and variants explained above.

With the above and other objects in view there is also provided, in accordance with the invention, a powder-metallurgy process of producing a molding, such as an interconnector or an end plate of an electrochemical cell. The process comprises the following steps:

a) providing a powder batch which, based on the total metal content, has a chromium content of ≥80% by weight and in which at least a portion of the chromium-containing powder has a BET surface area of ≥0.05 m²/g, in particular ≥0.07 m²/g, preferably ≥0.25 m²/g;

b) pressing the powder batch to form a compact (in particular at a pressing pressure in the range of from 500 to 1000 MPa);

c) sintering the compact at from 1100 to 1500° C. (preferably in a hydrogen atmosphere).

The entire Cr portion of the molding is preferably provided by a powder produced according to the invention. For cost reasons, however, it can also be advantageous to mix powder having a BET surface area of ≥0.05 m²/g, which has been produced in particular by the process according to the invention, with conventional powder (e.g. produced by aluminothermic means), whereby sufficient stability and good pressability can likewise still be achieved.

According to a further development of the invention, presintering of the compact at from 500 to 1000° C. (preferably under a hydrogen atmosphere) is carried out between the pressing step (step B) and the sintering step (step C). According to a further development, a pressing aid (e.g. a wax) is added to the powder batch in an amount of from 0.1% by weight to 5% by weight, based on the amount of powder batch, before pressing.

According to a further development, the molding obtained after the sintering step (step C) is oxidized (at a temperature in the range of from 800 to 1050° C.) in the presence of an oxygen source (e.g. $O_2$, $H_2O$, $CO_2$ or mixtures thereof; other oxygen sources may also be possible) and then the oxide layer is removed from at least part of the surface of the molding.

According to a further development, the pressing step (step B)) is the only pressing operation carried out during production of the molding. In the case of conventional powders, it is generally necessary to carry out two pressing operations in order to achieve the required precision of the contours. By using chromium-containing powders which have a BET surface area of ≥0.05 m²/g, in particular chromium-containing powders which have been produced according to the invention, a precise configuration of the contours can be achieved in a single pressing operation and at comparatively low pressing pressures. An additional advantage is comparatively low production costs.

As an alternative to one-stage production (i.e. with only one pressing step), it is also possible within the scope of production by powder metallurgy to provide two pressing steps. In the latter case, a calibration pressing operation at a pressing pressure in the range of from 500 to 1000 MPa is in particular carried out between the presintering step and the sintering step (step C)). As a result, homogenization of the density ratios in the molding is achieved in particular.

According to a further development, the above-mentioned process according to the invention is applied to produce a chromium-containing powder and added at least proportionately to the powder mixture. The metal powder according to the invention can be produced by reduction of at least one compound from the group consisting of chromium oxide and chromium hydroxide, optionally with an added solid carbon source, under the at least temporary exposure of hydrogen and hydrocarbon. Suitable as the chromium oxide or chromium hydroxide are in preferably Cr(III) compounds in powder form, for example $Cr_2O_3$, CrOOH, $Cr(OH)_3$ or, naturally, mixtures of chromium oxides and chromium hydroxides. The preferred chromium source is $Cr_2O_3$ (preferably of pigment grade).

Preferably, the compound from the group consisting of chromium oxide and chromium hydroxide, optionally with an added solid carbon source, is heated to a temperature $T_R$ of 1100° C.≤$T_R$≤1550° C., preferably to a temperature $T_R$ of 1200° C.≤$T_R$≤1450° C., and optionally held at that temperature. While very long holding times at $T_R$ are required in the lower temperature range in order to establish an advantageous degree of reduction of 90%, in the upper temperature range the holding time can be chosen to be very short or can be omitted altogether. The total pressure of the reaction is advantageously from 0.95 to 2 bar. Advantageously, the hydrocarbon is present in the form of $CH_4$. Preferably, at least during the heating operation, the hydrocarbon partial pressure is from 5 to 500 mbar at least temporarily. The residual gas atmosphere is preferably hydrogen.

The exposure of hydrogen and hydrocarbon preferably takes place at least in the temperature range from 800° C. to 1050° C. The hydrocarbon partial pressure is preferably in a range of from 5 to 500 mbar in that temperature range. The reaction mixture that forms from the starting materials is preferably in that temperature range for at least 45 minutes, particularly preferably for at least 60 minutes. That time includes both the heating operation and any isothermal holding phases in that temperature range. With the process conditions according to the invention it is ensured that at temperatures of preferably <$T_R$, the hydrocarbon reacts partially with at least one compound selected from the group consisting of chromium oxide and chromium hydroxide, in the presence of hydrogen, to form chromium carbide. Preferred chromium carbides are $Cr_3C_2$, $Cr_7C_3$ and $Cr_{23}C_6$. The at least partial formation of chromium carbide which occurs above the hydrocarbon partial pressure has an advantageous effect on the powder properties. With the described process conditions it is further ensured that the chromium carbide reacts with the chromium oxide and/or chromium hydroxide present in the reaction mixture or newly added thereto to form chromium (Cr), this process being dominant at $T_R$.

The hydrocarbon can be added to the reaction in gaseous form, preferably without the admixture of a solid carbon source. The compound from the group consisting of chromium oxide and chromium hydroxide is preferably reduced under the at least temporary exposure of an $H_2$—$CH_4$ gas mixture. Advantageously, an $H_2$/$CH_4$ volume ratio in the range of from 1 to 200, particularly advantageously from 1.5 to 20, is chosen. The exposure of the $H_2$—$CH_4$ gas mixture preferably takes place at least temporarily during the heating phase to $T_R$, the influence on the formation of the powder form being very advantageous in particular in the temperature range from 850 to 1000° C. If a temperature of approximately 1200° C. is reached, the atmosphere is preferably changed to a pure hydrogen atmosphere, preferably with a dew point of <−40° C. (measured in the region of the gas supply). If $T_R$ is below 1200° C., the changeover to the pure hydrogen atmosphere preferably takes place when $T_R$ is reached. The isothermal phase at $T_R$ and cooling to room temperature advantageously take place in a hydrogen atmosphere. In particular during cooling, it is advantageous to use hydrogen with a dew point <−40° C. in order to avoid reoxidation.

In one variant embodiment, a solid carbon source is mixed with the chromium oxide and/or chromium hydroxide. From 0.75 to 1.25 mol, preferably from 0.90 to 1.05 mol, of carbon are preferably used per mol of oxygen in the chromium compound. The amount of carbon available for the reaction with the chromium compound is thereby meant. In a particularly preferred variant embodiment, the ratio O to C, at approximately 0.98, is slightly sub-stoichiometric. The solid carbon source is preferably selected from the group carbon black, active carbon, graphite, carbon-releasing compounds or mixtures thereof. An example of a carbon-releasing compound which may be mentioned is chromium carbides, such as, for example, $Cr_3C_2$, $Cr_7C_3$ and $Cr_{23}C_6$. The powder mixture is heated to $T_R$ in an $H_2$-containing atmosphere. The $H_2$ pressure is preferably so adjusted that a $CH_4$ partial pressure of from 5 to 500 mbar is obtained at least in the temperature range from 800° to 1050° C. The isothermal phase at $T_R$ and cooling to room temperature are again advantageously carried out in a hydrogen atmosphere. The presence of hydrocarbon is not necessary during this phase of the process. Hydrogen prevents re oxidation processes in this phase of the process and during the cooling phase. During the cooling phase, a hydrogen atmosphere with a dew point <-40° C. is preferably used.

Other features which are considered as characteristic for the invention are set forth in the appended claims.

Although the invention is illustrated and described herein as embodied in a powder metallurgical molding, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 1:
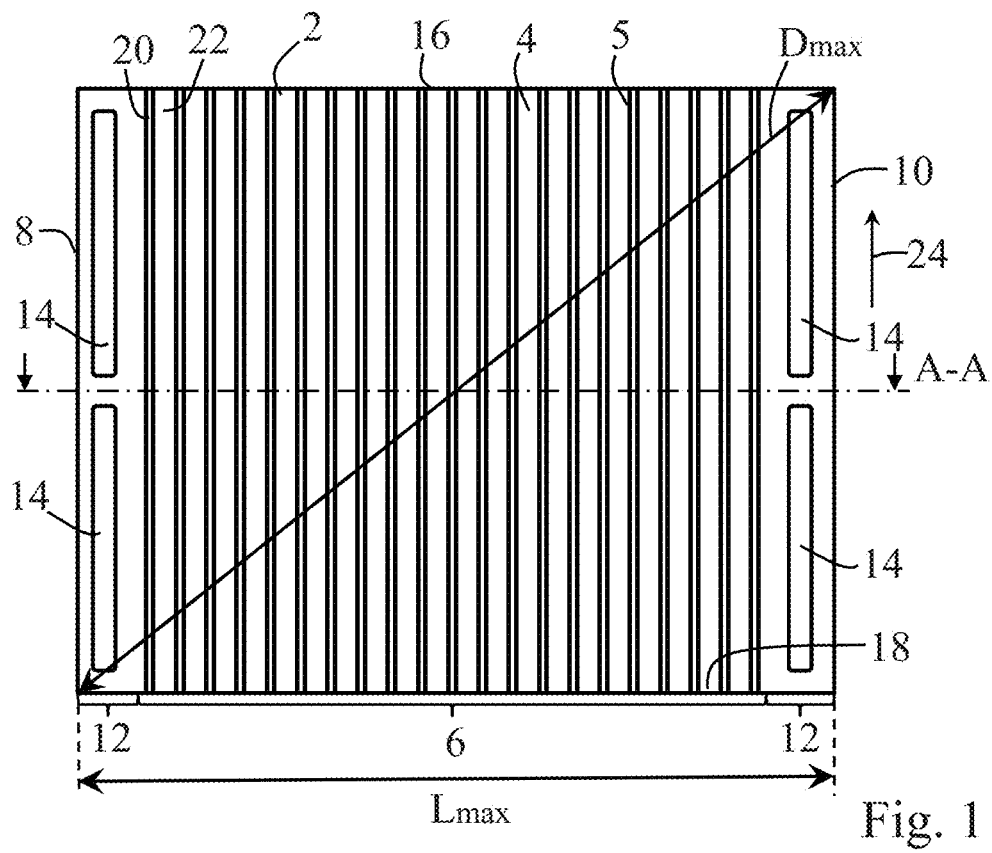
FIG. 1 shows a top view of an interconnector of co-flow design.
Figure 2:
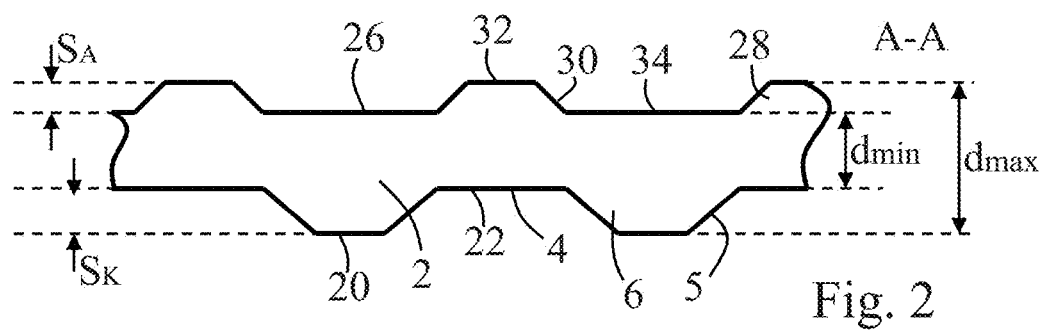
FIG. 2 is a cross-sectional view of a section of the interconnector of FIG. 1.

Referring now to the figures of the drawing in detail and first, particularly, to FIG. 1 thereof, there is shown a top view of a main face 4 of a (rectangular) interconnector 2 of co-flow design. The main face 4 is delimited by four circumferential side edges 8, 10, 16, 18. On the main face 4 shown, the interconnector 2 has precisely one flow field 6 with a structuring 5 formed in the interconnector 2. Adjacent to the flow field 6 on each of two mutually opposite sides there is an edge region 12, which extends to the side edges 8 or 10. Slot-like through-openings 14 for supplying and conveying away the process gases are provided in each of the edge regions 12. On the remaining two sides, the flow field 6 extends to the respective side edges 16, 18. The flow field 6 has a plurality of ridge-shaped elevations 20 with intermediate depressions 22 which extend continuously, substantially parallel to one another, along a main extension direction 24 from one side edge 16 to the opposite side edge 18 of the interconnector 2 (shown only schematically in FIG. 1). The flanks of the ridge-like elevations 20 each fall away obliquely towards the depressions 22 (see FIG. 2). FIG. 2 shows a cross-sectional view (along the cut surface A-A shown in FIG. 1) of a section of the interconnector 2 shown in FIG. 1 in the region of the flow field 6. On the opposite main face 26 there is likewise formed in a corresponding manner precisely one flow field 28 with a structuring 30 which has a plurality of ridge-like elevations 32 with intermediate depressions 34. Edge regions (not shown) are again provided adjacent to the side edges 8, 10. The main extension directions 24 of the structuring 5, 30 of both main faces 4, 26 run parallel to one another (co-flow design), the depressions 22 of one main face 4 each being arranged opposite the elevations 32 of the other main face 26 and vice versa (arrangement at gaps).

As is apparent with reference to FIG. 2, the structural depth $S_A$ of the opposite main face 26, which during use faces, for example, an anode of an adjacent fuel cell, is lower in the present case than the structural depth $S_K$ of the main face 4 shown in FIG. 1, which during use faces, for example, a cathode of an adjacent fuel cell. The maximum diameter $D_{max}$ measured along the main face 4 or 26 corresponds in the case of the shape of the interconnector 2 shown to the spacing between two opposite corners, as is shown in FIG. 1. Here, the term diameter is used in its broadest meaning as straight line passing from side to side through the center of a body or a figure. In a rectangle, the maximum diameter is the diagonal, in a round body it is the longest straight line from one side to an opposite side. The side length of the longest side edge $L_{max}$ is likewise shown in FIG. 1. The thickness of the core region, which is not affected by the structuring 5, 30, in the region of the flow fields 6, 28 is substantially constant over the main faces 4, 26 in the interconnector 2 shown and thus corresponds to the minimum thickness $d_{min}$ (see FIG. 2). In the embodiment shown, the maximum thickness $d_{max}$ of the interconnector 2 corresponds to the spacing of the elevations 20, 32 in the region of the flow fields 6, 28, projected onto a thickness direction running perpendicular to the plane of the main faces 4, 26, and is constant over the region of the flow fields 6, 28 (see FIG. 2).

Figure 3:
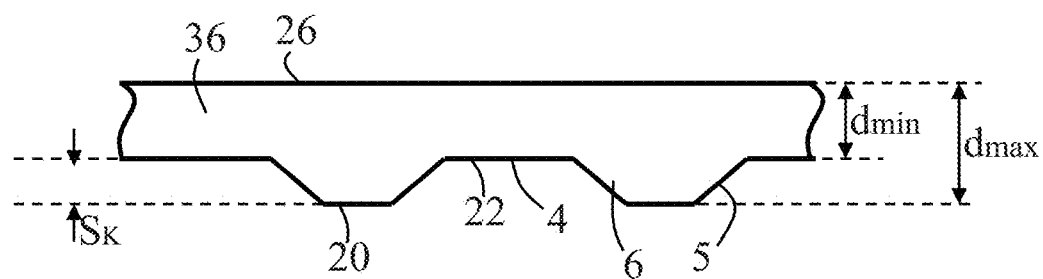
FIG. 3 shows a cross-sectional view of a section of an end plate.

FIG. 3 shows a cross-sectional view of a section of an end plate 36. The end plate 36 has a flow field 6 with a structuring 5 in a corresponding manner to that explained in relation to FIGS. 1 and 2 on only one main face 4, which (in the embodiment shown) faces the cathode of an adjacent fuel cell during use. Accordingly, the same reference numerals as in FIGS. 1 and 2 have been used in FIG. 3 for corresponding component sections, and reference is made to the explanations relating to FIGS. 1 and 2. In contrast to FIGS. 1 and 2, the core region is followed by a structuring 5 in the region of the flow field 6 on only one side, so that the minimum thickness $d_{min}$ of the core region and the maximum thickness $d_{max}$ of the end plate 36 are each measured along the thickness direction from the depressions 22 or elevations 20 to the opposite main face 26 (see FIG. 3).

Exemplary embodiments for the production of interconnectors according to the present invention are explained herein below. Interconnectors having different geometries were thereby produced, all of which had a ratio $D_{max}/d_{min}$ in the range $140 \leq D_{max}/d_{min} \leq 350$ and at the same time exhibited sufficient stability. In particular, interconnectors having the dimensions indicated below were produced.

| No.: | Length [mm] | Width [mm] | $d_{max}$ [mm] | $d_{min}$ [mm] | $D_{max}/d_{min}$ |
|---|---|---|---|---|---|
| 1 | 100 | 100 | 1.8 | 0.89 | 158.9 |
| 2 | 110 | 110 | 1.8 | 0.9 | 172.8 |
| 3 | 180 | 180 | 2.5 | 1.0 | 254.6 |
| 4 | 200 | 160 | 2.5 | 1.0 | 256.1 |
| 5 | Main face round: diameter: 200 mm | | 2.5 | 1.0 | 200.0 |

Obtaining Chromium Powder Having a Large BET Surface Area:

500 g of $Cr_2O_3$ of pigment grade (Lanxess Bayoxide CGN-R) having a mean particle size $d_{50}$, measured by means of laser diffraction, of 0.9 μm (for powder morphology see FIG. 3) were heated in the course of 80 min. to 800° C. in $H_2$ (75% by volume)-$CH_4$(25% by volume) (flow rate 150 l/h, pressure approximately 1 bar). Thereafter, the reaction mixture was heated slowly to 1200° C., the reaction mixture being in the temperature range from 800 to 1200° C. for 325 min. The reaction mixture was then heated in the course of 20 min. to $T_R$, where $T_R$=1400° C. The holding time at 1400° C. was 180 min. Heating from 1200° C. to $T_R$ and holding at $T_R$ were carried out with the supply of dry hydrogen with a dew point <−40° C., the pressure being approximately 1 bar. Furnace cooling was likewise carried out under $H_2$ with a dew point <−40° C. There was obtained a metallic sponge which could very easily be deagglomerated to a powder.

Powder Batch:

A powder batch consisting of 95% by weight fine Cr powder (having a BET surface area of ≥0.05 m²/g, granulated to form a more readily pourable powder having a particle size fraction of 45-250 μm, e.g. produced by the process for obtaining chromium powder explained above) and 5% by weight of an FeY master alloy (alloy with 0.8% by weight Y, particle size <100 μm) is then prepared. 1% by weight of pressing aid (wax) is added to the powder batch. This mixture is then mixed for 15 min in a tumbling mixer.

Exemplary Embodiment Single Pressing Operation:

This mixture is introduced into a mold and pressed at a specific pressing pressure of from 500 to 1000 MPa (in the present case e.g. at 800 MPa), so that a compact is formed. The compact is then presintered at from 500 to 1000° C. (in the present case e.g. at 900° C.) for 20 min (time at maximum temperature) under a hydrogen atmosphere in a conveyor furnace for the purpose of dewaxing the compact. After presintering, high-temperature sintering of the component is carried out at from 1100° C. to 1450° C. (in the present case e.g. at 1450° C.) for from 1 to 7 h (time at maximum temperature; in the present case e.g. for 7 h) under a hydrogen atmosphere for the purpose of further densification and alloy formation. Oxidation of the component is then carried out at 950° C. for a period of from 10 to 30 h (in the present case e.g. for 20 h; h: hour) in order to close up any residual porosity to such an extent that the permeability is sufficiently low. The surface of the oxidized component is freed of the oxide layer by a sand-blasting process on all sides.

Exemplary Embodiment Two Pressing Operations:

The advantages of and further information regarding the two-stage pressing operation are described, for example, in U.S. Pat. No. 8,173,063 B2. Obtaining the chromium powder and production of the powder batch are carried out as explained above. Production of the compact, including the pressing step and the presintering step, are carried out as in the exemplary embodiment single pressing operation above. After presintering, calibration pressing of the presintered component is carried out at a specific pressing pressure of from 500 to 1000 MPa (in the present case e.g. at 800 MPa). High-temperature sintering, oxidation and processing by a sand-blasting process are then carried out in a corresponding manner to the exemplary embodiment single pressing operation.

In relation to the pressing pressure in the pressing step, it should be added that, when a powder having a large BET surface area (in particular 0.05 m²/g) is used, and in particular when a sponge-like powder is used, as can be produced, for example, by the process according to the invention (see in particular the process for obtaining chromium powder explained above), significantly better pressability is obtained and lower pressing pressures are accordingly sufficient. This is advantageous in view of the production costs and also in view of minimal wear of the pressing tools. While a typical pressing pressure of >900 MPa (MPa: megapascal) is used in the case of a maximum thickness in the region of the flow field/fields of 2.5 mm and in the case of conventional chromium powder produced by aluminothermic methods, a pressing pressure of 600 MPa is sufficient when using the advantageous powder for a maximum thickness of both 2.5 mm and 2.2 mm. In the case of a maximum thickness in the region of the flow field/fields of 2.0 mm and of 1.8 mm, a pressing pressure of only 500 MPa was sufficient when using the advantageous powder.

Figure 4:
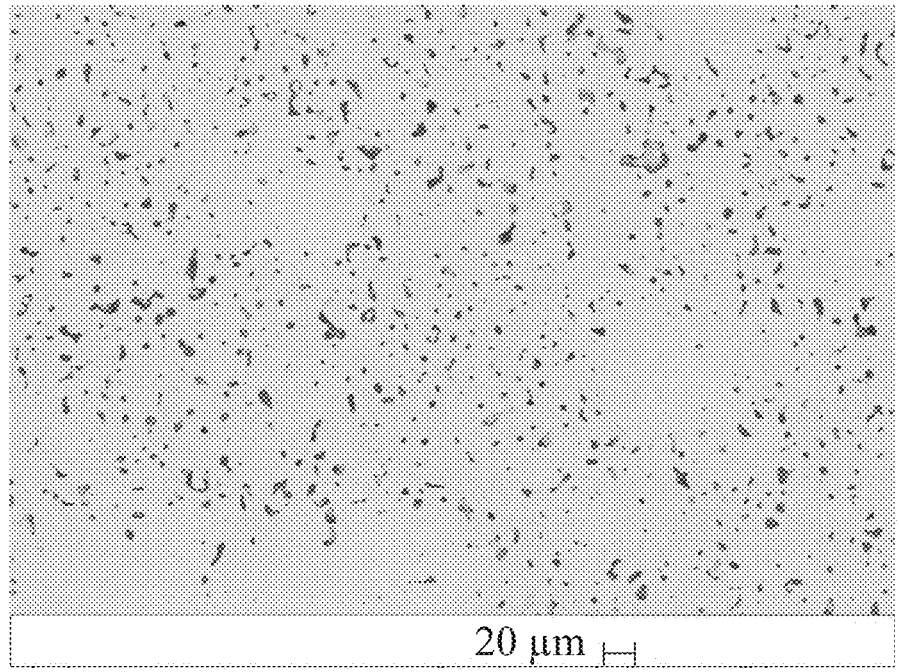
FIG. 4 shows a scanning electron microscope image of an interconnector with an advantageous microstructure.
Figure 5:
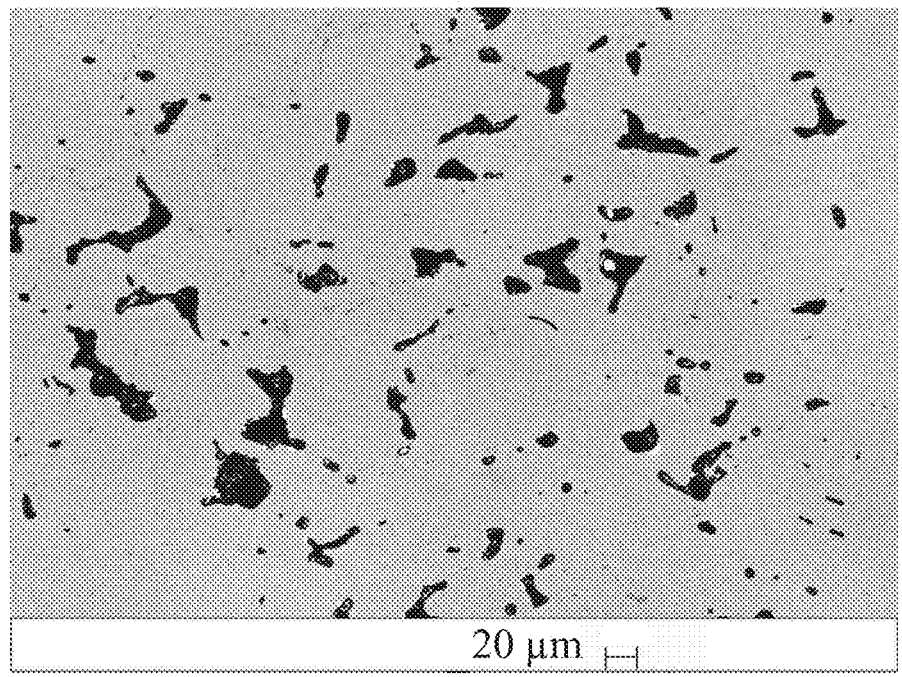
FIG. 5 shows a scanning electron microscope image of an interconnector with a conventional microstructure.

Furthermore, when a powder having a large BET surface area (in particular ≥0.05 m²/g) is used, and in particular when a sponge-like powder is used, as can be produced, for example, by the process according to the invention (see in particular the process for obtaining chromium powder explained above), the molding has a particularly advantageous microstructure, as is explained below with reference to FIGS. 4 and 5. FIG. 4 shows a scanning electron microscope image of a cross-sectional ground section of an interconnector which has such an advantageous microstructure. By comparison, FIG. 5 shows a corresponding image of an interconnector produced by conventional means (using chromium powder produced by aluminothermic means) on the same scale. The pores that are empty or partly filled with metal oxide(s) and also the oxide inclusions are significantly darker in these images than the surrounding metallic matrix. As is apparent with reference to FIGS. 4 and 5, the advantageous microstructure is distinguished by a finely divided pore pattern. The proportion of large pores (pores that are empty or partly filled with metal oxide(s)) and oxide inclusions is especially very small. In particular—based on a specific minimum size of the pores that are empty or partly filled with metal oxide(s) and of oxide inclusions—the proportion by surface area thereof, relative to the total surface area of pores that are empty or partly filled with metal oxide(s) and of oxide inclusions, is significantly smaller in the case of the advantageous microstructure than in the case of interconnectors produced by conventional means, as is shown by the following table (evaluated by means of the quantitative image analysis described below):

|  | Minimum size | | |
| --- | --- | --- | --- |
|  | ≥100 μm² | ≥70 μm² | ≥50 μm² |
| Conventional interconnector | 88% | 92% | 94% |
| Interconnector produced with novel powder | 5% | 14% | 24% |

Description of the Quantitative Image Analysis for Determining the Microstructure For the quantitative image analysis, the moldings were cut perpendicularly to their main face by means of a diamond wire saw into segments having an edge length of approximately 20 mm. The cut surface was located through the flow field(s). The blanks were cleaned with water and then dried. The dried blanks were embedded in epoxy resin. After a curing time of at least 8 hours, the cut edges of the samples were prepared metallographically, that is to say an examination over the thickness of the component can later be carried out. The preparation comprises the steps:

grinding at from 150 to 240 N with firmly bonded SiC paper of grit sizes 240, 320, 400, 800, 1000, 1200 and 2400 grit;

fine grinding with 9 μm $Al_2O_3$ lapping paper;

polishing with diamond suspensions, first with 3 μm grain size and then with 1 μm grain size;

final polishing with a diamond suspension of grain size 0.04 μm;

cleaning of the specimens in an ultrasonic bath;

drying of the specimens.

Five images of different, representative areas of the ground surface were then prepared for each specimen, the areas each being chosen within the core region. This was carried out by means of scanning electron microscopy ("Ultra Plus 55" from Zeiss) using a 4-quadrant annular detector to detect back-scattered electrons (BSE). The excitation voltage was 20 kV, the tilt angle was 0°. The images were focussed; the resolution should be at least 1024×768 pixels for correct image analysis. The contrast was so chosen that both the pores and any partial metal oxide fillings of the pores as well as oxide inclusions clearly stand out from the metallic matrix and—as explained above—can be evaluated together. The magnification for the images was so chosen that each image contains at least 100 pores/oxide inclusions. In the present case, this gave image areas of from 0.04 to 0.25 mm².

The quantitative image analysis was carried out using "QWin" software from Leica. The "QXCount" module was used. Each image analysis followed the steps:

setting a grey level threshold so that pore volume in the pores that is open and possibly partly filled with metal oxide(s), and also oxide inclusions (i.e. without open pore volume) were detected together as "pore/oxide inclusion";

fixing the measure frame, in this case the entire image area;

measurement options: classification by equivalent diameter;

detection adjustment: dark objects, fill holes, remove edge particles, open reconstruct.

Filter functions should not be used either in the image or in the analysis of the images. Because the "pores/oxide inclusions" (as defined above) appear darker in a back scattered electron image than the metallic matrix, the "dark objects" must be defined as "pores/oxide inclusions" (as defined above) in the detection adjustment. It can occur, for example owing to partial filling of the pore volume with metal oxide(s), that this combination of pore volume and metal oxide filling is not detected as an object and is thus detected as an "area" (for the evaluation of the area sizes of the pores/oxide inclusions explained above). The option "fill holes" is to be used in order to detect this combination, and thus its area, as an associated object. By means of the option "remove edge particles", incomplete "pores/oxide inclusions" (as defined above) in the edge region of the image area are not included in the evaluation.

After the 5 images had been analyzed individually in each case, a statistical evaluation of the data of all 5 images was carried out. The following parameters were used for this evaluation:

proportion by surface area of the pores (%)

density (1/mm²) of the pores/oxide inclusions (as defined above)

equivalent diameter (μm) of the individual pores/oxide inclusions area (μm²) of the individual pores/oxide inclusions.

The invention claimed is:

1. A powder metallurgical molding for an electro-chemical cell, the molding comprising:

a plate having a basic plate shape with two main faces;

said plate being formed with a chromium content of at least 80% by weight and being configured as an interconnector for a solid oxide fuel cell (SOFC);

each of said main faces having:

a flow field formed on each of said main faces, said main face having, in a region of said flow field, a structuring with a plurality of knob-shaped or ridge-like elevations and intermediate depressions;

an edge region laterally of the respective said flow field and surrounding the respective said flow field completely or partially;

wherein a ratio of a maximum diameter $D_{max}$ of the molding, measured along the main face, to a minimum thickness $d_{min}$ of a core region of the molding that extends along the flow field(s) and is not affected by the structuring lies in a range of $140 \leq D_{max}/d_{min} \leq 350$; and wherein a maximum thickness $d_{max}$ of the molding in the region of said flow field is ≤2.3 mm (millimeters).

2. The molding according to claim 1, wherein the minimum thickness $d_{min}$ of the core region of the molding is ≤1.1 mm (millimeters).

3. The molding according to claim 1, wherein the maximum diameter $D_{max}$ of the molding, measured along the main face, is ≥200 mm.

4. The molding according to claim 1, wherein precisely one said flow field is formed on each of said two main faces of the molding.

5. The molding according to claim 1, wherein a ratio of a size of the main face in mm² (square millimeters) to the minimum thickness $d_{min}$ of said core region in mm (millimeters) is $\geq 1.3 \times 10^4$ mm.

6. The molding according to claim 1, wherein a ratio of a total weight of the molding in g (grams) to a size of the main face in cm² (square centimeters) is ≤1.1 g/cm².

7. The molding according to claim 1, wherein one or more flow fields are formed on each of said two main faces of the molding, and said structuring of mutually opposite flow fields have main extension directions along the respective said main faces running substantially parallel to one another.

8. The molding according to claim 1, wherein said plate is formed with four circumferential side edges, said four circumferential side edges including two mutually opposite side edges running parallel to one another, and wherein a ratio of a side length $L_{max}$ of a longest side edge to the minimum thickness of the core region $d_{min}$ is greater than or equal to 110.

9. The molding according to claim 1, wherein, in the core region, a proportion by surface area of pores that are empty or partly filled with metal oxide and of oxide inclusions which have a surface area of ≥100 μm² (square micrometers), relative to a total surface area of pores that are empty or partly filled with metal oxide and of oxide inclusions, is 60%, evaluated by quantitative image analysis on a scanning electron microscope image of a measurement area which is located in a cut surface, running along a thickness direction, through the molding into the core region.

10. The molding according to claim 1, wherein, in the core region, a proportion by surface area of pores that are empty or partly filled with metal oxide and of oxide inclusions which have a surface area of ≥70 μm² (square micrometers), relative to a total surface area of pores that are empty or partly filled with metal oxide and of oxide inclusions, is ≤70%, evaluated by quantitative image analysis on a scanning electron microscope image of a measurement area which is located in a cut surface, running along a thickness direction, through the molding into the core region.

11. The molding according to claim 1, wherein, in the core region, a proportion by surface area of pores that are empty or partly filled with metal oxide and of oxide inclusions which have a surface area of ≥50 μm² (square micrometers), relative to a total surface area of pores that are empty or partly filled with metal oxide and of oxide inclusions, is ≤80%, evaluated by quantitative image analysis on a scanning electron microscope image of a measurement area which is located in a cut surface, running along a thickness direction, through the molding into the core region.

12. The molding according to claim 1, wherein, in the core region, a proportion by surface area P of pores that are empty or partly filled with metal oxide and of oxide inclusions, provided they lie wholly within a measurement area under consideration, relative to a total surface area of the measurement area, lies in a range of 80%≤(1−P)≤95%, evaluated by means of quantitative image analysis on a scanning electron microscope image of the measurement area which is located in a cut surface, running along a thickness direction, through the molding into the core region.

13. The molding according to claim 1, wherein the core region is formed with a uniform distribution of pores that are empty or partly filled with metal oxide and of oxide inclusions, and wherein, in the core region, a mean spacing λ of the pores that are empty or partly filled with metal oxide and of the oxide inclusions is ≤9 μm, wherein the mean spacing λ is calculated according to the formula $$\lambda = \left(\frac{\frac{4}{3}\pi a^3}{P}\right)^{\frac{1}{3}},$$

wherein:
  2a corresponds to a mean equivalent pore or oxide inclusion diameter;
  P is a proportion by surface area of pores that are empty or partly filled with metal oxide and of oxide inclusions, provided they lie wholly within a measurement area; and
  values for 2a and P are evaluated by quantitative image analysis on a scanning electron microscope image of a measurement area that is located in a cut surface, running along the thickness direction, through the molding into the core region.

14. A method for producing a powder metallurgical molding according to claim 1, the method comprising:
  a) providing a powder batch which, based on a total metal content, has a chromium content of ≥80% by weight and in which at least a portion of the powder batch has a BET surface area of ≥0.05 m²/g;
  b) pressing the powder batch to form a compact; and
  c) sintering the compact at a temperature from 1100 to 1500° C.;
  to form the molding according to claim 1.

15. The method according to claim 14, wherein the pressing step (b) is the only pressing operation carried out during the production of the molding.

16. The method according to claim 14, which comprises presintering the compact at a temperature from 500 to 1000° C. between the pressing step (b) and the sintering step (c).

17. The method according to claim 14, which comprises oxidizing the molding obtained after the sintering step (c) in the presence of an oxygen source to form an oxide layer, and subsequently removing the oxide layer from at least part of a surface of the molding.

18. The method according to claim 14,
  wherein the providing step (a) comprises producing a chromium-containing powder having a BET surface area of ≥0.05 m²/g and a chromium content of ≥90% by weight by reduction of at least one compound selected from the group consisting of chromium oxide and chromium hydroxide, optionally with an added solid carbon source, under an at least temporary exposure of hydrogen and hydrocarbon and adding the chromium-containing powder at least proportionately to the powder batch.

* * * * *